United States Patent
Poquet et al.

(10) Patent No.: US 6,994,997 B1
(45) Date of Patent: Feb. 7, 2006

(54) GRAM POSITIVE BACTERIA DEPRIVED OF HTRA PROTEASE ACTIVITY AND THEIR USES

(75) Inventors: Isabelle Poquet, Paris (FR); Alexandra Gruss, Orsay (FR); Alexandre Bolotine, Nancy (FR); Alexei Sorokine, Gif-sur-Yvette (FR)

(73) Assignee: Institut National de la Recherche Agronomique, Paris (FR)

( * ) Notice: Subject to any disclaimer, the term of this patent is extended or adjusted under 35 U.S.C. 154(b) by 0 days.

(21) Appl. No.: 09/869,106

(22) PCT Filed: Dec. 23, 1999

(86) PCT No.: PCT/FR99/03270

§ 371 (c)(1),
(2), (4) Date: Oct. 9, 2001

(87) PCT Pub. No.: WO00/39309

PCT Pub. Date: Jul. 6, 2000

(30) Foreign Application Priority Data

Dec. 24, 1998 (FR) ................................. 98 16462

(51) Int. Cl.
*C12P 21/04* (2006.01)
(52) U.S. Cl. .................... 435/71.1; 435/69.1; 435/243; 435/252.3; 435/252.9; 435/253.4; 424/234.1; 424/200.1; 424/244.1; 424/246.1
(58) Field of Classification Search ............. 424/234.1, 424/200.1, 244.1, 246.1; 435/69.1, 71.1, 435/243, 252.3, 252.9, 253.4
See application file for complete search history.

(56) References Cited

U.S. PATENT DOCUMENTS 5,264,365 A    11/1993  Georgiou et al. ........ 435/252.8

FOREIGN PATENT DOCUMENTS

| WO | 91/02064    | * 2/1991 |
| WO | 92/02064    | * 2/1991 |
| WO | WO 91/15572 |   10/1991 |
| WO | 97/38587    | * 10/1997 |
| WO | WO 88/05821 |   8/1998 |

OTHER PUBLICATIONS

Buist et al. J. Bacteriol. Nov. 1998. 1998. 180(22): 5947-5953.*
Bayles et al. Abstracts of the 97th Gen.Meeting of the ASM. May 4-8, 1997, p. 363. K-129.*
Smeds et al., 1998, Journal of Bacteriology, v. 180, No. 23, p. 6148-6153.
Pallen et al., 1997, Molecular Microbiology, 26(2), p. 209-221.

* cited by examiner

*Primary Examiner*—Jennifer E. Graser
(74) *Attorney, Agent, or Firm*—Morgan, Lewis & Bockius (57) ABSTRACT

The invention concerns bacteria strains, obtained from gram-positive bacteria whereof the genome size is not more than 3.2 Mb, and wherein the HtrA surface protease is inactive. Said strains are useful for expressing exported proteins of interest.

4 Claims, 9 Drawing Sheets

```
                                            PRIMER G
    aaacaagatgaaaacatgatttatcaacattttttttactttttttccacttttctgtggaa
  1 ---------+---------+---------+---------+---------+---------+60 aactttattaaaatatccacttatcctcattaattttttagattatccacaaaaatgtgga
 61 ---------+---------+---------+---------+---------+---------+120
              -35                  -10                    -10
    gaaactatattagtttgatttttgttactattaaggtattattaagtgagagtagatata
121 ---------+---------+---------+---------+---------+---------+180
                                                   RBS
    attacatcatagaaatgctacaaagattaataattgaaaggaattatttatggcaaaagc
181 ---------+---------+---------+---------+---------+---------+240
                                                       M  A  K  A
                                            PRIMER F
    taatataggaaaattgctattaacaggtgtcgtgggcggagccatcgcacttggaggaag
241 ---------+---------+---------+---------+---------+---------+300
     N  I  G  K  L  L  L  T  G  V  V  G  G  A  I  A  L  G  G  S
                     TRANSMEMBRANE DOMAINE
    tgcaatctatcaaagcactacaaatcaatcggcaaataatagtcgttcaaatacaactag
301 ---------+---------+---------+---------+---------+---------+360
     A  I  Y  Q  S  T  T  N  Q  S  A  N  N  S  R  S  N  T  T  S tacaaaggttagtaacgtttcggtaaatgtcaataccgatgttacctctgcaattgaaaa
361 ---------+---------+---------+---------+---------+---------+420
     T  K  V  S  N  V  S  V  N  V  N  T  D  V  T  S  A  I  E  K agtttcaaattctgtcgtttctgttatgaattatcaaaaagataactcacaaagtagtga
421 ---------+---------+---------+---------+---------+---------+480
     V  S  N  S  V  V  S  V  M  N  Y  Q  K  D  N  S  Q  S  S  D cttcagttcaattttttggtggaaatagcggttcaagttcatcgactgatggcttacagct
481 ---------+---------+---------+---------+---------+---------+540
     F  S  S  I  F  G  G  N  S  G  S  S  S  S  T  D  G  L  Q  L ttctagtgaaggctctggtgtcatctacaaaaaatctggtggtgatgcctacgttgtaac
541 ---------+---------+---------+---------+---------+---------+600
     S  S  E  G  S  G  V  I  Y  K  K  S  G  G  D  A  Y  V  V  T
                                              CATALYTIC DOMAINE
    taactaccacgttattgctggtaatagctcacttgatgttctgctttctggtggacaaaa
601 ---------+---------+---------+---------+---------+---------+660
     N  Y  H  V  I  A  G  N  S  S  L  D  V  L  L  S  G  G  Q  K
```

FIG. 1

```
       agtcaaagattctgtggttggttatgatgaatacacagaccttgctgttcttaaaatcag
661 ---------+---------+---------+---------+---------+---------+720
        V  K  D  S  V  V  G  Y  D  E  Y  T │D  L  A  V  L  K  I  S│
                                            CATALYTIC DOMAINE
       ttctgaacatgtcaaagatgtggcgacattcgctgattctagtaaattaacaattggtga
721 ---------+---------+---------+---------+---------+---------+780
        S  E  H  V  K  D  V  A  T  F  A  D  S  S  K  L  T  I  G  E acctgccattgccgttggctcacctttaggtagtcaatttgcaaacaccgcaactgaagg
781 ---------+---------+---------+---------+---------+---------+840
        P  A  I  A  V  G  S  P  L  G  S  Q  F  A  N  T  A  T  E  G aattttatctgcaacaagccgtcaagtgactttgacccaagaaaatggtcaaacaactaa
841 ---------+---------+---------+---------+---------+---------+900
        I  L  S  A  T  S  R  Q  V  T  L  T  Q  E  N  G  Q  T  T  N
                                       PRIMER A
       tatcaatgcaattcaaacagatgctgccattaaccctggtaactctggagggctttgat
901 ---------+---------+---------+---------+---------+---------+960
        I  N  A  I  Q  T  D  A  A  I  N  P │G  N  S  G  G  A  L  I
                                            CATALYTIC DOMAINE
       taatattgaaggacaagttattggaattactcaaagtaaaattacaacaactgaagatgg
961 ---------+---------+---------+---------+---------+---------+1020
       │N  I  E  G  Q  V  I  G  I  T│ Q  S  K  I  T  T  T  E  D  G ttctacttctgtcgaaggtttaggatttgcgattccttctaatgatgtcgtaaatatcat
1021---------+---------+---------+---------+---------+---------+1080
        S  T  S  V  E  G  L  G  F  A  I  P  S  N  D  V  V  N  I  I taataaacttgaagatgatggtaagatttcacgccctgctttaggtatccgaatggttga
1081---------+---------+---------+---------+---------+---------+1140
        N  K  L  E  D  D  G  K  I  S  R  P  A  L  G  I  R  M  V  D cctttcacaattatcaacaaatgacagttctcaattgaaattactaagcagtgtaacagg
1141---------+---------+---------+---------+---------+---------+1200
        L  S  Q  L  S  T  N  D  S  S  Q  L  K  L  L  S  S  V  T  G tggggttgttgtttactccgtccaatctggacttcctgctgcctcagctggtttgaaagc
1201---------+---------+---------+---------+---------+---------+1260
        G  V  V  V  Y  S  V  Q  S  G  L  P  A  A  S  A  G  L  K  A tggagatgtaattacaaaggttggcgatacagcagtaacctcttcaacagacttgcaaag
1261---------+---------+---------+---------+---------+---------+1320
        G  D  V  I  T  K  V  G  D  T  A  V  T  S  S  T  D  L  Q  S
```

FIG. 1
(CONTINUED)

```
      tgctctttactcacacaatatcaatgatacagtaaaagttacttattatcgtgatggtaa
1321 ─────────+─────────+─────────+─────────+─────────+─────────+ 1380
       A  L  Y  S  H  N  I  N  D  T  V  K  V  T  Y  Y  R  D  G  K atcaaatacagcagatgttaaactttctaaatcaaccagtgacttagaaacaagcagtcc
1381 ─────────+─────────+─────────+─────────+─────────+─────────+ 1440
       S  N  T  A  D  V  K  L  S  K  S  T  S  D  L  E  T  S  S  P atcttcttctaattaataacttaataatttaataaaagtcttctgtaaatagaaggcttt
1441 ─────────+─────────+─────────+─────────+─────────+─────────+ 1500
       S  S  S  N tttcatactaaagtctgaaattttaaaaataataaatttccattttctttattgatt
1501 ─────────+─────────+─────────+─────────+─────────+─────────+ 1560 tatggtaaaataaagttaagcatgaaaatttactttacttagaagccgaacaattttg
1561 ─────────+─────────+─────────+─────────+─────────+─────────+ 1620 agtcattcaggaattggtcgtgcaatgaaacatcaacaacgcgcccttgatttaatgggc
1621 ─────────+─────────+─────────+─────────+─────────+─────────+ 1680 attgactggacaaaaaatcctgaggatgattacgatatcctccatttaaatacttatggc
1681 ─────────+─────────+─────────+─────────+─────────+─────────+ 1740
```

GRAM POSITIVE BACTERIA DEPRIVED OF HTRA PROTEASE ACTIVITY AND THEIR USES

The invention relates to the production, in Gram-positive bacteria, of exported proteins.

The general term "exported proteins" denotes proteins which are transported across the cytoplasmic membrane. In the case of Gram-positive bacteria, this transport results in the secretion of the protein into the medium, or its association with the cell surface.

One of the main problems which arises during the production of exported proteins of interest by host bacteria lies in the degradation of these proteins during and/or after their exportation, at the cell envelope or at the cell surface. This degradation often leads to a decrease in the yield, and/or a modification of the structure and of the activity of the protein.

The enzymes responsible for this degradation of exported proteins are bacterial proteases, themselves exported in the envelope; they are "housekeeping" proteases, one of the main functions of which is normally a role of degradation of abnormal or incorrectly folded exported proteins which accumulate in the medium or in the envelope, in particular under conditions of stress, and the role of which is also the recycling of exported proteins.

Heterologous proteins, which are often incompletely recognized by the chaperone proteins involved in protein folding in the host bacterium, are particularly sensitive to attack by these proteases.

The oldest characterized exported housekeeping protease is the *E. coli* serine protease HtrA/DegP. It is a protease which as a periplasmic location, and which is expressed under the control of a promoter which is inducible at high temperature; Beckwith and Strauch (Proc. Natl. Acad. Sci. USA 85:1576–1580, 1988) have observed that it is involved in the proteolysis of proteins made from fusion between exported proteins of *E. coli* and the PhoA exportation reporter. They have proposed the inactivation of this protease in *E. coli* in order to limit the degradation of the heterologous exported proteins.

Mutant *E. coli* strains, in which the gene encoding the HtrA/DegP protease has been inactivated, have thus been obtained [Beckwith and Strauch, abovementioned publication, and PCT application WO 88/05821]; however, it has been noted that this inactivation results in a slowing down of the kinetics of degradation, but is not sufficient to abolish it because of the existence, in the envelope, of other proteases which degrade the exported proteins.

In *E. coli* several envelope housekeeping proteases, which carry out functions similar to those of HtrA/DegP, have been characterized: they are in particular the HhoA/DegQ and HhoB/DegS proteases, which are structurally homologous to HtrA/DegP, and proteases which are structurally different but functionally comparable (ApeA/proteaseI, OmpT, OmpP, Prc/Tsp, SppA/proteaseIV, PrtIII and SohB).

Studies relating to other bacteria have also made it possible to demonstrate the existence, in each species studied, of several exported housekeeping proteases. For example, a large number of bacterial species have several proteases of the HtrA family (Pallen and Wren, Mol. Microbiol. 19:209–21, 1997); three homologues of HtrA have been identified in *B. subtilis* (YyxA, YkdA and YvtB/Yirf), *Synechocystis* (HtrA, HhoA and HhoB), *Pseudomonas aeruginosa* and *Aquifex aeolicus*, two in *Hemophilus influenzae* (HtoA and HhoB), *Campylobacter jejuni*, *Brucella abortus* and *Yersinia enterolitica*, and four in *Mycobacterium tuberculosis*. Various Gram-positive bacteria also have serine proteases considered to be related to the HtrA family on the basis of homology in the catalytic domain: EtA, EtB and V8/StsP of *S. aureus*, GseP of *Bacillus licheniformis* and Spro of *Mycobacterium paratuberculosis* (Koonin et al., Chap 117 in *Escherichia coli* and *Salmonella typhimurium*, 2203–17, 1997). Finally, exported proteases which are not related to HtrA have also been demonstrated, for example in *B. subtilis* (Margot and Karamata, Microbiology, 142:3437–44, 1996; Stephenson and Harwood Appl. Environ. Microbiol. 64:2875–2881, 1998; Wu et al. J. Bacteriol. 173:4952–58, 1991).

It has therefore been proposed to combine mutations affecting several exported proteases in order to obtain an effective decrease in the degradation of heterologous exported proteins.

For example, an *E. coli* strain mutated in the degP/htrA, ompT, prt and prc genes (Meerman and Georgiou, Bio/technology 12:1107–10, 1994), and a *B. subtilis* strain deficient in the six extracellular proteases (Wu et al., 1991, abovementioned publication), have been constructed with this aim. However, the use of these strains does not make it possible to completely eliminate the proteolysis of the exported proteins. For example, in the case of the *B. subtilis* strain described by Wu et al., although the residual extracellular protease activity is negligible (<1%), degradation of the heterologous exported proteins remains significant. In order to overcome this problem, that same team has carried out further modifications to this strain in order to make it overproduce various chaperones (Wu et al., J. Bacteriol. 180:2830–35, 1998). Furthermore, although the inactivation of the gene of one of these exported housekeeping proteases does not have any notable consequences for the bacterium, the accumulation of mutations may affect strain viability; Meerman and Georgiou (1994, abovementioned publication) thus observe a decrease in growth rate which can range up to 50%.

In lactic acid bacteria, only a few exported proteases have been studied; the most well characterized at the present time is the protease named PrtP (Kok, FEMS Microbiol. Reviews 87:15–42, 1990), which is located at the cell surface, where it is anchored to the peptidoglycan. This protease is present in many lactic acid bacteria, in particular *Lactococcus lactis*, and is located on a plasmid. It contributes to the nitrogen-based nutrition of bacteria by degrading milk caseins. Other surface proteases have been purified from two species of lactic acid bacteria, *Lactobacillus delbrueckeii* subsp. *bulgaricus* and *Lactobacillus helveticus*, but their function has not been determined (Stefanitsi et al., FEMS Microbiol. Lett. 128:53–8, 1995; Stefanitsi and Garel, Lett. Appl. Microbiol. 24:180–84, 1997; Yamamoto, et al., J. Biochem. 114:740–45, 1993). A stress-induced gene encoding a protein which is highly homologous to the proteases of the HtrA family has recently been revealed in *Lactobacillus helveticus* (Smeds et al., J. Bacteriol. 180:6148–53, 1998). It has been observed that this gene is necessary for survival at high temperature; a mutant *Lactobacillus helveticus* strain in which the htrA gene has been inactivated by insertion of a reporter gene (gusA, encoding β-glucuronidase) under the control of the htrA promoter, was constructed. The study of the expression of the gusA gene in this mutant made it possible to demonstrate induction of the transcription of this gene under the same conditions as that of the htrA gene in the wild-type strains; on the other hand, no β-glucuronidase activity was observed.

In previous investigations directed towards studying exported proteins of *Lactococcus lactis* by studying proteins fused with the Δ$_{SP}$Nuc exportation reporter (Poquet et al., J. Bacteriol. 180:1904–12, 1998), the team of inventors has observed significant extracellular proteolysis even though the experiments were carried out in an *L. lactis* subsp. *cremoris* strain free of any plasmid and therefore, in particular, of that which carries prtP.

BRIEF DESCRIPTION OF THE DRAWINGS

FIG. 2A shows the growth of htrA⁺/htrA, htrA, and IL1403 strains at 30° C. FIG. 2B shows the growth of htrA⁺/htrA, htrA, and IL1403 strains at 37° C.

The inventors undertook to investigate extracellular proteases responsible for this proteolysis.

They have thus discovered, in *L. lactis*, the existence of a gene of the htrA family.

This gene, detected in the genome of the IL1403 strain of *L. lactis* subsp. *lactis*, encodes a 408 amino acid protein, hereinafter named HtrA$_{L1}$, the nucleotide sequence and the amino acid sequence of which are represented on FIG. 1, and appear in the attached sequence listing (SEQ ID NO: 1). This protein is very homologous to *E. coli* HtrA, and to various other known members of the HtrA family, as shown in table I below, which illustrates the percentages of identity and of similarity between HtrA$_{L1}$ and various proteins of the HtrA family:

TABLE I

| Protein | Organism | % identity | % similarity |
|---|---|---|---|
| HtrA/DepP/Do protease | *E. coli* | 31.5 | 38.2 |
| HhoA/DegQ | *E. coli* | 34.0 | 40.8 |
| HhoB/DegS | *E. coli* | 29.9 | 37.3 |
| HtrA | *S. typhimurium* | 32.4 | 39.1 |
| HtoA | *H. influenzae* | 31.9 | 39.2 |
| HhoB/DegS | *H. influenzae* | 31.2 | 40.0 |
| spHtrA | *S. pneumoniae* | 55.6 | 62.0 |
| HtrA | *Lb. helveticus* | 46.9 | 54.1 |
| YyxA | *B. subtilis* | 43.5 | 52.0 |
| YkdA | *B. subtilis* | 42.5 | 49.4 |

The HtrA protein of the IL1403 strain of *L. lactis* subsp. *lactis* has the three amino acids Ser, His and Asp, which define the catalytic site characteristic of serine proteases related to trypsin, among which is the HtrA family; in addition, it has, around these three amino acids, the following three motifs: DAYVVTNYH$_{127}$VI, D$_{157}$LAVLKIS, and GNS$_{239}$GGALINIEGQVIGIT, which correspond to the consensus regions defined by Pallen and Wren (Mol. Microbiol. 19:209–21, 1997) for the catalytic domain of the HtrA proteases: -GY--TN-HV-, D-AV---- and GNSGG-L-N-G--IGIN.

At its N-terminal end, it has a hydrophobic amino acid sequence L$_{10}$LTGVVGGAIALGGSAI$_{26}$ corresponding to a putative transmembrane segment. The HtrA$_{L1}$ protein of *L. lactis* subsp. *lactis* is therefore thought to be an integral protein of the cytoplasmic membrane. According to the "positive inside" rule concerning the topology of these proteins (Von Heijne, Nature, 341:456–8, 1989), it topology corresponds to the "C-out" type, i.e. its C-terminal portion, which comprises in particular its catalytic site, would be exposed to the outside of the plasma membrane. Like the HtrA protease of *E. coli*, *L. lactis* subsp. *lactis* HtrA$_{L1}$ therefore appears to be an envelope protease which can degrade exported proteins. The amino acids of the catalytic domain and of the transmembrane domaine are framed on FIG. 1.

The inventors have inactivated this gene by mutation; at optimum temperature (30° C.), the mutant *L. lactis* subsp. *lactis* strain thus obtained is viable and grows normally; on the other hand, its growth and viability are affected at higher temperatures (from 37° C.), both on plates and in liquid medium.

In addition, the inventors have studied the effect of this mutation on the exportation of various fusion proteins, and have noted that the inactivation of the HtrA$_{L1}$ protease in *L. lactis* is sufficient to completely abolish the degradation of the exported proteins; this effect is surprising given the residual proteolysis observed previously in other bacteria after inactivation on proteases of the HtrA family.

A subject of the present invention is a process for producing a protein of interest, characterized in that it comprises culturing a bacterial strain which expresses said protein of interest, and which can be obtained from a Gram-positive bacterium, the size of the genome of which bacterium is at most equal to 3.2 Mb, preferably at most equal to 3 Mb, and advantageously at most equal to 2.5 Mb, by mutation which inactivates the HtrA surface protease of said bacterium;

and producing said protein of interest exported by said strain.

According to a preferred embodiment of the present invention, the starting Gram-positive bacterium is chosen from bacteria of the group consisting of the Streptococcaceae, and Lactobacillaceae. Advantageously, it is chosen from lactococci.

It may be also be chosen from bacteria belonging to the group consisting of the Bacillaceae, for example to the *Listeria* genus, and the Enterococcaceae, in particular of the *Enterococcus* genus.

Advantageously, said bacterial strain may also comprise one or more other modifications of its genome, directed toward improving the production and/or secretion of proteins expressed in said bacterium, and/or toward avoiding their degradation. Depending on the type of protein intended to be produced, it is possible, for example, to use a bacterial strain in which the PrtP protease activity has been inactivated, and/or a bacterial strain which overproduces a protein allowing the stabilization of exported proteins, such as the Nlp4 protein of *Lactococcus lactis*, or a homologue thereof (Poquet et al. 1998, abovementioned publication).

A subject of the present invention is also any bacterial strain which can be obtained from a Gram-positive bacterium, the size of the genome of which bacterium is at most equal to 3.2 Mb, as defined above, by mutation which inactivates the HtrA surface protease of said bacterium, and which also comprises at least one cassette for expressing a gene of interest, with the exception of a *Lactobacillus helveticus* strain comprising a single expression cassette consisting of the sequence encoding the gusA reporter gene inserted into the htrA gene of said strain, under the transcriptional control of the promoter of said gene.

The term "expression cassette" is intended to mean any recombinant DNA construct comprising a gene of interest, the expression of which is desired, or a site allowing the insertion of said gene, placed under the control of regulatory sequences for transcription (promoter, terminator), which are functional in the host bacterium under consideration.

For the purpose of the present invention, the term "HtrA protease" is intended to mean any serine protease of the trypsin type, having functional and structural similarities with the HtrA protease of *E. coli* which are sufficient for it to be included in the same family, i.e.:
  a catalytic site formed by the three amino acids Ser, His and Asp;
  the presence, around this catalytic site, of the consensus regions: -GY--TN-HV-, D-AV---- and GNSGG-L-N-G-IGIN;
  an exportation signal enabling the protease to be transported to the cell surface of the bacterium, (it may, for example, be a signal peptide, a transmembrane domain, a signal for anchorage to the wall, etc.).

In order to implement the present invention, mutant bacteria lackiing HtrA activity can be produced by carrying out one or more mutations, in particular in the sequence encoding the HtrA protease and/or in the regulatory sequences allowing the expression of the htrA gene, so as to prevent the expression of a functional HtrA protease. These mutations can be carried out conventionally, by deletion, insertion or replacement of at least one nucleotide or one nucleotide sequence in the htrA gene; they can result either in the absence of production of HtrA, or in the production of an HtrA protease in which at least one amino acid required for activity has been deleted or replaced.

The suitable mutagenesis techniques are known per se; advantageously, use will be made of site-directed mutagenesis techniques, since the data available on the proteases of the HtrA family make it possible, even though more precise information on the specific sequence of the gene whose inactivation is desired is not available, to target the mutation(s) on conserved domains which are required for activity (for example the catalytic domain).

The present invention can be implemented in many domains.

Firstly, it can be used in the domain of the production of proteins of interest (for example enzymes, human proteins, etc.) by genetic engineering, using cultures of bacteria transformed with a gene of interest. In this domain, the present invention makes it possible to improve the yield of exported proteins (and in particular secreted proteins), and to avoid their contamination with inactive proteolytic products: this makes it possible to purify them easily and less expensively.

For this application, use will preferably be made of the mutant strains produced from nonpathogenic bacteria, such as *Lactococcus* spp. or *Lactobacillus* spp., and also food streptococci, *Streptococcus thermophilus*.

The mutant strains produced from bacteria conventionally used in the agro-foods industry, such as lactic acid bacteria (in particular lactococci, *lactobacilli* and thermophilic streptococci), can advantageously be used in this domain. For example, they can be used in the composition of ferments, in order to produce heterologous proteins making it possible to improve the quality of the finished fermented product; thus, the exportation of foreign enzymes produced by a mutant *L. lactis* strain in accordance with the invention, within cheeses fermented with *L. lactis*, may improve their maturing and their organoleptic qualities.

These mutant strains can also be used for producing dietetic products or medicinal products. In this domain, mutant strains in accordance with the invention can, for example, be used in order to express, prior to the ingestion of the product and/or after its ingestion, proteins with a prophylactic or therapeutic effect, such as enzymes (for facilitating digestion, for example), proteins for stimulating the immune system, immunization antigens, etc. In most cases, for use in this domain, and in order to guarantee maximum innocuity, mutant strains produced from nonpathogenic bacteria and, advantageously, from bacteria conventionally used for food will be preferred. However, in the context of uses for immunization, mutant strains produced from pathogenic bacteria (in particular streptococci, staphylococci, enterococci or *listeria*), and preferably from variants of these bacteria already carrying one or more mutations which attenuate their pathogenic power, can be used; the inactivation of the HtrA protein, in limiting the capacities of survival of these bacteria under conditions of stress, may contribute to attenuating their virulence, as previously observed in the case of certain Gram-negative bacteria.

In the context of certain applications, in which the host bacterium must be viable and capable of producing proteins at temperatures of about 35 to 40° C., for example the production, in a fermentor, of certain proteins, or the production, after ingestion, in the digestive tract of humans or animals, of proteins with therapeutic or prophylactic activity, mutant strains produced from thermophilic bacteria, such as *Streptococcus* thermophilus, will advantageously be used.

The present invention will be more clearly understood with the aid of the continuation of the description which follows, which refers to nonlimiting examples illustrating the production of *L. lactis* mutants in which the HtrA surface protease is inactive, and the properties of these mutants.

EXAMPLE 1

Inactivation of the hrtA Gene of *L. lactis* htrA gene, carried by the chromosome of the IL1403 strain (Chopin et al. Plasmid, 11, 260–263, 1984) of *L. lactis* subsp. *lactis*, was inactivated by integration of a suicide plasmid carrying a 665 bp internal fragment of the gene (FA).

As a positive control for integration, a suicide plasmid carrying a 902 bp fragment truncated in the 3' region (GA), the integration of which onto the chromosome restores a wild-type copy of the gene, was used.

These fragments were obtained beforehand by PCR amplification from the genomic DNA of the IL1403 strain of *L. lactis* subsp. *lactis*, using the pairs of primers F/A and G/A:

F[5'-GGAGCCA(G/T)(A/C/T)GC(A/G/C/T)(C/T)T(A/G/T)GG-3'] located downstream of the ATG initiation codon G[5'-GTTTCCACTTTTCTGTGG-3'] located upstream of the htrA promoter A[5'-TT(A/T)CC(A/T)GG(A/G)TT(A/G/T)AT(A/G/C/T)GC-3'] located upstream of the serine codon of the catalytic site.

Figure 1:
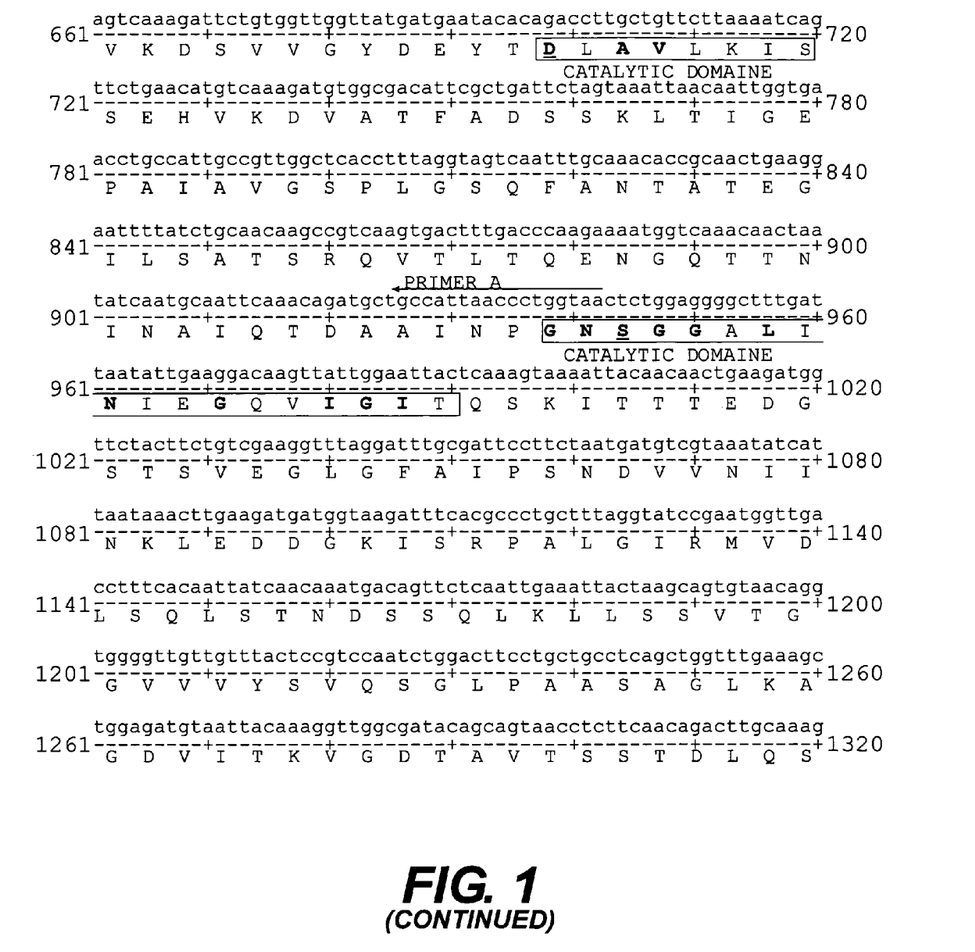
FIG. 1 shows the nucleotide and amino acid sequence of the gene HtrA$_{L1}$ (SEQ ID NO: 1). The amino acids of the catalytic domain and transmembrane domain are box framed. The positions of primers F, G, and A are indicated by arrows.

The positioning of the F, G and A primers is indicated on FIG. 1.

The amplification was carried out under the following conditions:

reaction mixture: 0.2 mM of each dNTP, 5 µM of each oligonucleotide, approximately 500 ng of chromosomal DNA, 2 mM of MgCl$_2$ and 1.25 units of Taq-DNA-pol (Boehringer Mannheim), in the Taq buffer provided by the manufacturer;

temperature conditions: 5 min 94° C. 30 cycles (30 sec at 94° C., 30 sec at 46° C., and 30 sec at 72° C.), and 4° C.

The amplified fragments were ligated to the linear pGEM$^T$ plasmid (Promega). After transformation of *E. coli* TG1 with the ligation products, the clones which are resistant to ampicillin and lack β-galactosidase activity are selected. The plasmids obtained, bearing the FA and GA fragments, respectively, are named pES1.1 and pES2.1.

The FA and GA inserts were subcloned into a suicide vector carrying a chloramphenicol resistance gene. Since this vector is incapable of replicating alone in the absence of the RepA protein which is required for initiating its replication, co-integrants were created by ligation between each of the pES1.1 and pES2.1 plasmids and the suicide vector, linearized beforehand.

After transformation of the *E. coli* TG1 strain, and selection of the chloramphenical-resistant clones, the pGEM$^T$ portion of the co-integrants was deleted and the vectors were re-circularized. The plasmids obtained are multiplied in the TG1 repA$^+$ strain of *E. coli*; after selection of the chloramphenicol-resistant clones, the suicide plasmids named pVS6.1 and pVS7.4 are obtained.

pVS6.1 contains the FA fragment, and pVS7.4 contains the GA fragment, of the htrA$_{L1}$ gene of the IL1403 strain of *L. lactis* subsp. *lactis*.

These plasmids were used to transform the IL1403 strain of *L. lactis* subsp. *lactis*; the clones which had integrated these plasmids at the htrA locus on the chromosome were selected in the presence of chloramphenicol.

In both cases, several independent chloramphenicol-resistant clones were obtained. Five clones of each class termed A to E in the case of the integration of pVS6.1, and 17 to 22 in the case of the integration of pVS7.4, were chosen for analysis.

For each of these clones, the integration at the htrA locus was confirmed by Southern transfer.

Two clones, A and 17, were chosen for the following analyses; they constitute the two prototypes of the mutant strains, which hereinafter will be named:

htrA (null mutation of the htrA$_{L1}$ gene, Cm$^R$); this strain does not express any active HtrA protease;

htrA$^+$/htrA (wild-type copy+truncated copy of the htrA$_{L1}$ gene, Cm$^R$); this strain expresses an active Htra$_{L1}$ protease.

EXAMPLE 2

Role of the htrA$_{L1}$ Gene of *L. lactis* in Survival at High Temperature

The two strains htrA and htrA$^+$/htrA are cultured, in liquid culture, under the conventional conditions for growth of *L. lactis*, i.e. at 30° C. and in the presence of oxygen, but without stirring, and in the presence of chloramphenicol. The behavior of the htrA strain of *L. lactis* subsp. *lactis* at 30° C. and at 37° C. was studied using the htrA$^+$/htrA strain and also the IL403 parent-strain (cultured in the absence of chloramphenicol) as control.

The bacteria were cultured overnight at room temperature, in an M17 medium containing 1% of glucose (+2.5 µg/ml of chloramphenicol for both the htrA strain and the htrA$^+$/htrA strain). The cultures were diluted 100-fold in the morning, in the same medium, and divided into two batches placed in semi-anaerobiosis at 30° C. or at 37° C. The growth was monitored by measuring the OD$_{600}$.

Figure 2A:
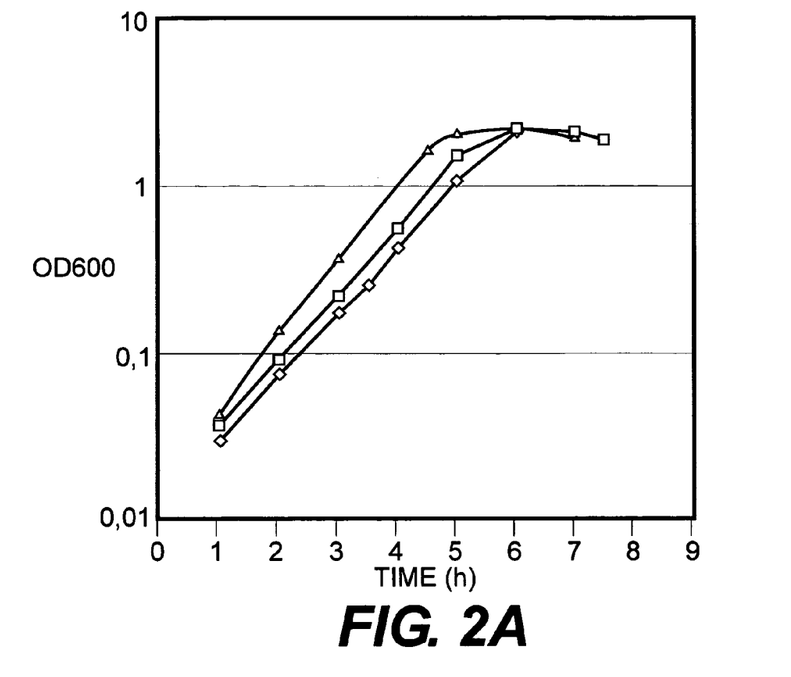
FIGS. 2A and B show the growth curves of the htrA⁺/htrA strain, htrA stain, and the wild-type IL1403 strain. The growth was monitored by measuring the OD$_{600}$ at the indicated time intervals.
Figure 2B:
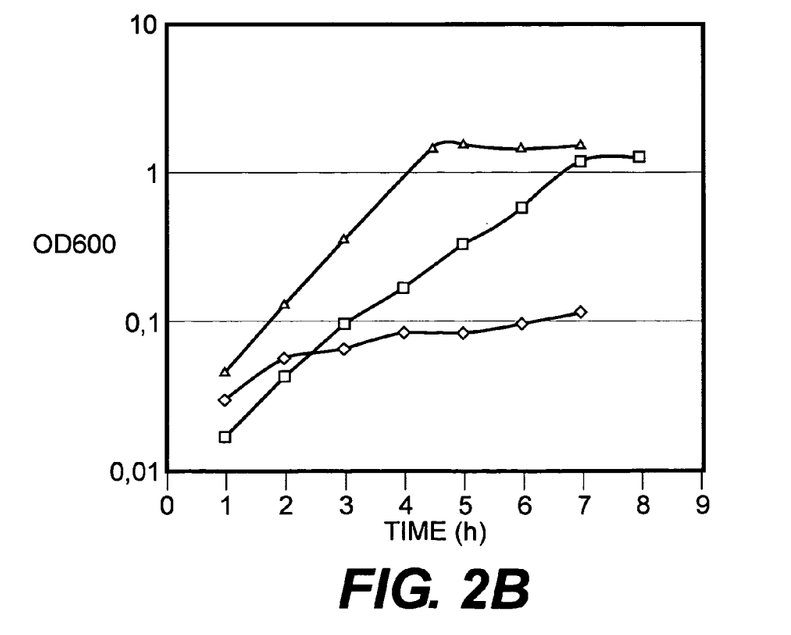

The results are illustrated in FIG. 2.

At 30° C. (FIG. 2A), it is noted that the htrA$^+$/htrA strain (■), the htrA strain (♦), and the wild-type IL1403 strain (▲) have very close generation times: 65 min for the wild-type strain, 70 min for htrA$^+$/htrA and 75 min for htrA; finally, for the 3 cultures, the OD$_{600}$ values corresponding to the stationary phase are very comparable (OD$_{600}$=2.1 to 2.2).

These results indicate that there is no significant difference in growth between these three strains at 30° C.

At 37° C. (FIG. 2B), the htrA$^+$/htrA strain (■) has a generation time of 100 min and the OD$_{600}$ of the stationary phase is less than at 30° C. (OD$_{600}$=1.25). Less growth at 37° C. than at 30° C. is also observed for the wild-type IL1403 strain (▲); the generation time is 65 min, but the OD$_{600}$ of the stationary phase is less than at 30° C. (OD$_{600}$=1.9). In the case of the htrA strain (◊), the growth is very slight, or even zero, and the OD$_{600}$ does not exceed 0.1, even after culturing for 7 h.

It emerges from these results that the htrA strain of *L. lactis* subsp. *lactis* is heat-sensitive and that the htrA mutation is lethal at 37° C.

EXAMPLE 3

Role of the htrA$_{L1}$ Gene of *L. Lactis* in Surface Proteolysis

The effect of the htrA$_{L1}$ mutation on the stability of five exported proteins was tested. These proteins are:

i) a heterologous protein, the secreted nuclease of *S. aureus*, Nuc; this protein is expressed by the plasmid pNuc3 (Le Loir et al., J. Bacteriol. 176:5135–5139, 1994; Le Loir et al., J. Bacteriol. 180:1895–903, 1998);

ii) three hybrid proteins (Usp-$\Delta_{SP}$Nuc, Nlp4-$\Delta_{SP}$Nuc and Exp5-$\Delta_{SP}$Nuc) resulting from the fusion between the $\Delta_{SP}$Nuc reporter and fragments of exported proteins of *L. lactis*: the secreted protein Usp45 (Van Asseldonk et al., Gene 95:155–60, 1990), the lipoprotein Nlp4 and the protein Exp5 (which is, itself, a protein made from fusion between an exported protein and a cytoplasmic protein); these proteins, and also the plasmids pVE8009, pVE8024 and pVE8021 which express them, respectively, are described by Poquet et al. (1998, abovementioned publication);

iii) a naturally exported protein of *L. lactis*, AcmA.

In the wild-type MG1363 strain of *L. lactis* subsp. *cremoris*, Usp-$\Delta_{SP}$Nuc is secreted and Nlp4-$\Delta_{SP}$Nuc is associated with the cells; for these two proteins, various degradation products, among which the NucA peptide originating from the $\Delta_{SP}$Nuc portion of the fusion, are detected in the medium, along with the mature form; with regard to the Exp5-$\Delta_{SP}$Nuc tripartite fusion, it is very unstable and the mature form is not detected in the medium, only the degradation products, including the NucA peptide. The mature form, and also the degradation products of these three hybrid proteins, can be detected using anti-NucA antibodies.

The naturally exported protein of *L. lactis* chosen is the bacteriolysin AcmA (Buist et al., J. Bacteriol. 177:1554–1563, 1995). This protein, which degrades peptidoglycan, is both secreted and associated with the surface, probably by affinity with its substrate. It provides, both in the MG1363 strain of *L. lactis* subsp. *cremoris* and the IL1403 strain of *L. lactis* subsp. *lactis*, proteolysis products which are active and therefore detectable, like the intact protein, by zymogram.

The strains transformed with the plasmids expressing these various proteins are cultured at 30° C. for several hours, at least up to the middle of the exponential phase or up to the start of the stationary phase.

For each plasmid, cultures of the three strains IL1403, hrtA and htrA$^+$/htrA, which had reached comparable OD$_{600}$ values, were used to extract protein samples: a) from the total culture, b) from the cells and c) from the medium, according to the protocol described by Poquet et al. (1998, abovementioned publication).

These samples are subjected to electrophoresis (SDS-PAGE) on denaturing gel.

In order to detect the Nuc, USP-$\Delta_{SP}$Nuc, Nlp4-$\Delta_{SP}$Nuc and Exp5-$\Delta_{SP}$Nuc proteins and their degradation products, the proteins are transferred onto a membrane, followed by immunological revelation using anti-NucA antibodies, which are detected using a protein G/peroxidase conjugate (BIO-RAD) and a chemiluminescence kit (Dupont-Nen).

AcmA is detected by zymogram (Buist et al., 1995, abovementioned publication): micrococci, in which the wall is sensitive to AcmA, are included in the electrophoresis gel at the concentration of 0.2%, which makes it opaque; after electrophoresis, the gel is treated at 37° C. overnight in a buffer containing 50 mM of Tris/HCl at pH 7 and 0.1% of Triton X100, which allows lysis of the micrococci by AcmA or its active proteolytic products. The gel is then colored with methylene blue at 0.1% in 0.01% KOH: the bands corresponding to the AcmA activity appear as transparent hydrolysis halos on a blue background.

For each protein, the degradation profiles in the IL1403, htrA and htrA$^+$/htrA strains were compared by observing the protein content accumulated during culturing for several hours.

FIGS. 3 to 6 show, respectively, the results of immunological detection for the Nuc, Usp-$\Delta_{SP}$Nuc, Nlp4-$\Delta_{SP}$Nuc and Exp5-$\Delta_{SP}$Nuc proteins. For the Nuc (FIG. 3) and Usp-$\Delta_{SP}$Nuc (FIG. 4) proteins, [lacuna]

Figure 7:
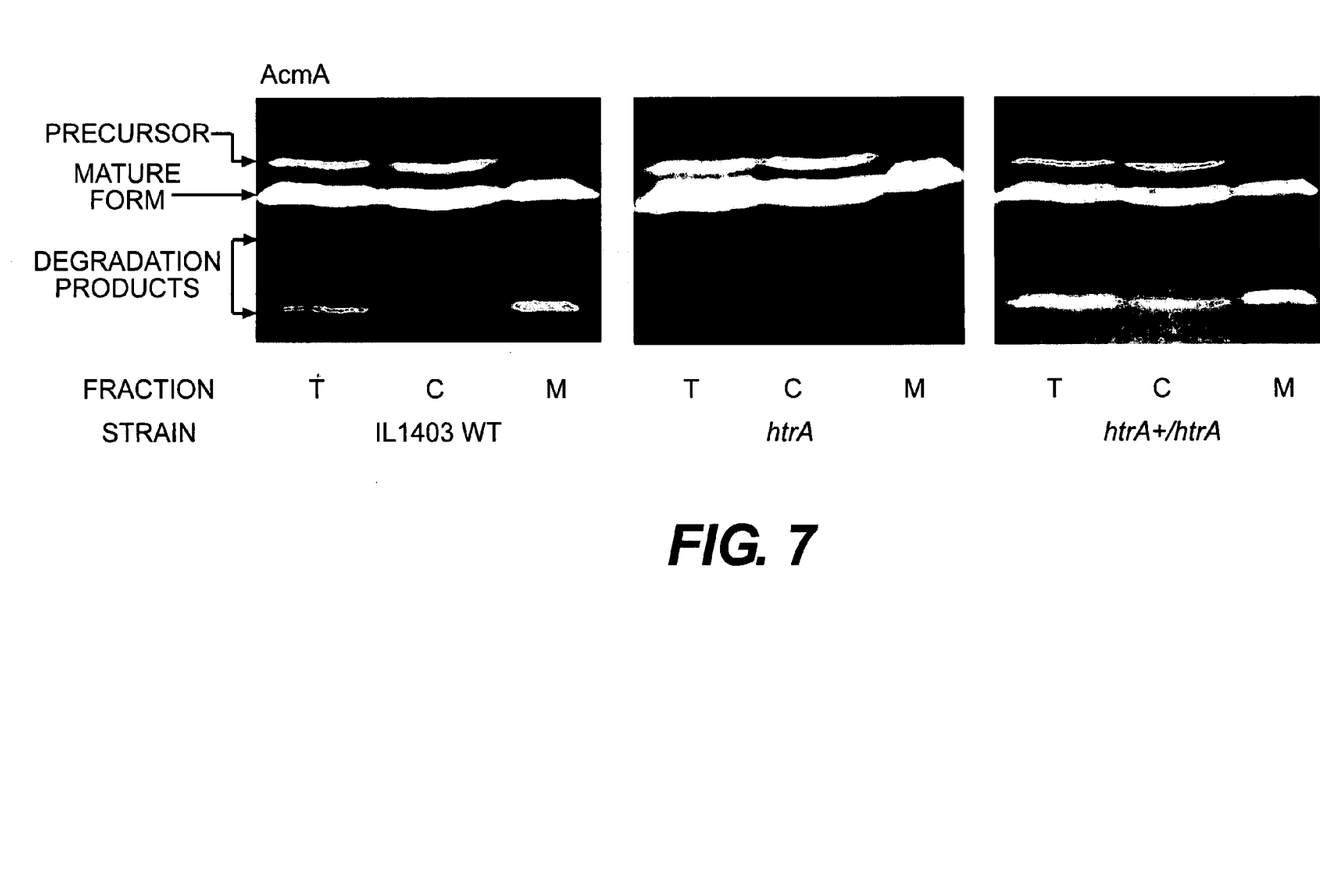
FIG. 7 shows a zymogram of the bacteriolysin activity of AcmA protein. The degradation profiles of AcmA protein in IL1403 (first three wells), htrA (three central wells) and htrA⁺/htrA (last three wells) strains are shown. The detection of the AcmA protein was carried out on the protein samples extracted from the total culture (T), cells alone (C) and from the medium (M) of each strain.

FIG. 7 represents a zymogram of the bacteriolysin activity of AcmA; the detection was carried out on the total culture (T), the cells alone (C) or the medium (M).

Figure 3:
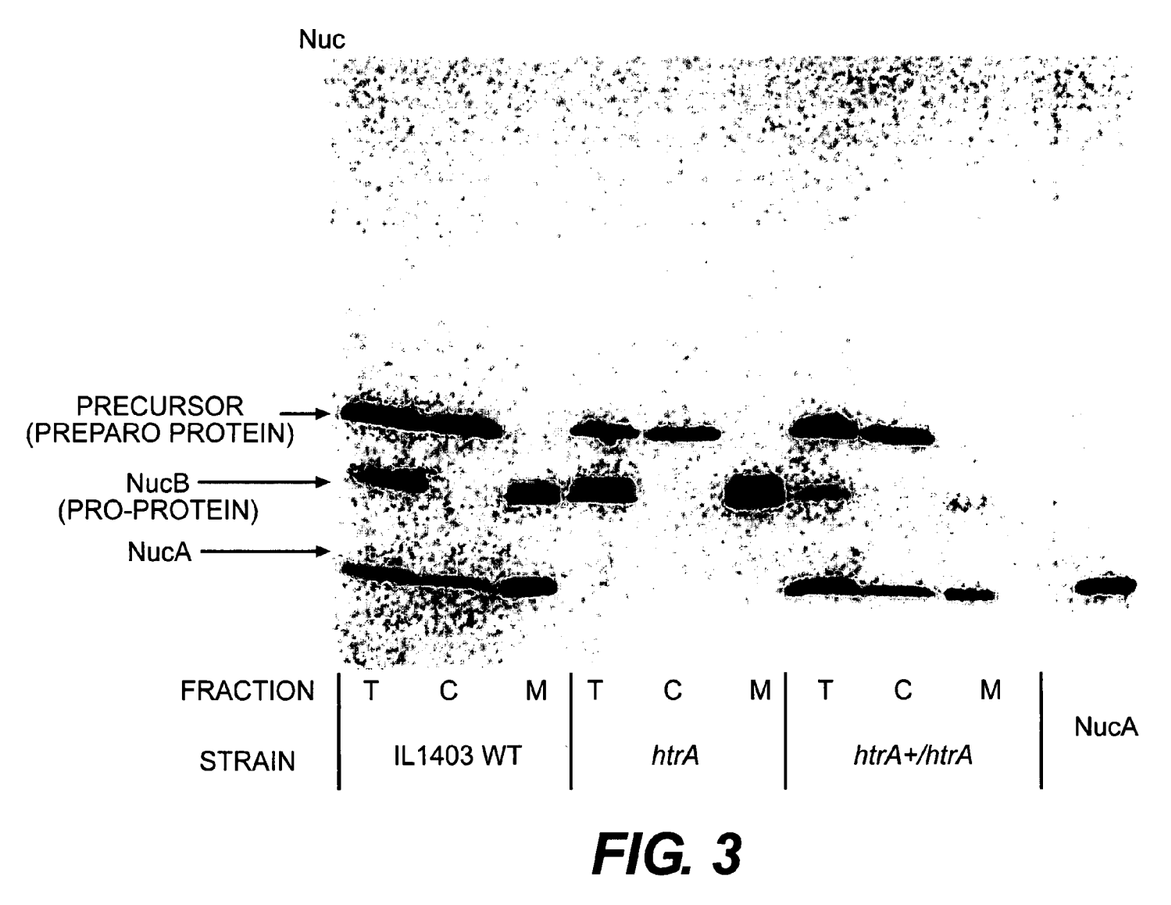
FIG. 3 shows the effect of HtrA$_{L1}$ mutation on the stability of Nuc protein. The degradation profiles of Nuc protein in IL1403 (first three wells), htrA (three central wells) and htrA⁺/htrA (last three wells) strains are shown. The immunological detection of the Nuc protein was carried out on the protein samples exacted from the total culture (T), cells alone (C) and from the medium (M) of each strain.
Figure 4:
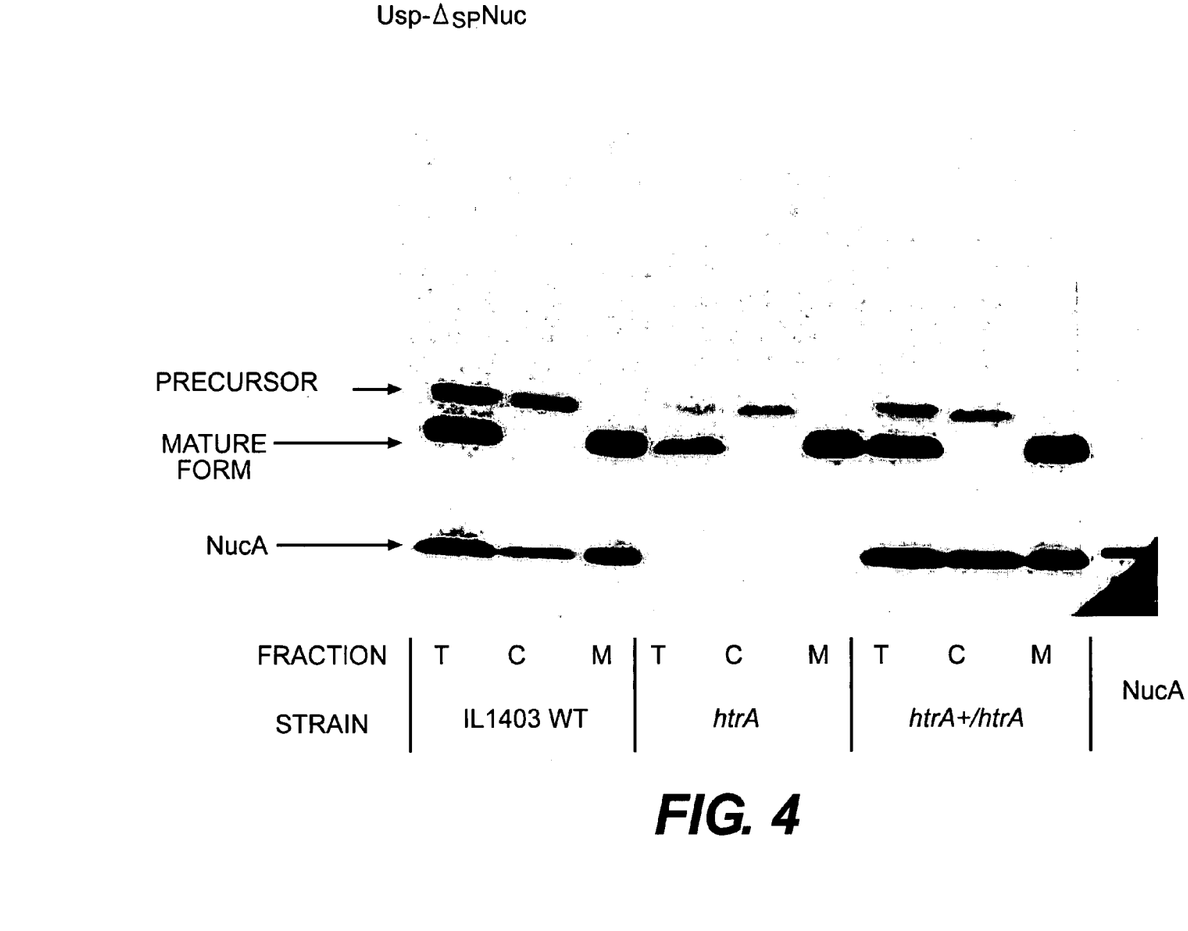
FIG. 4 shows the effect of HtrA$_{L1}$ mutation on the stability of Usp-Δ$_{SP}$Nuc protein. The degradation profiles of Usp-Δ$_{SP}$Nuc protein in IL1403 (first three wells), htrA (three central wells) and htrA⁺/htrA (last three wells) strains are shown. The immunological detection for the Usp-Δ$_{SP}$Nuc protein was carried out on the protein samples extracted from the total culture (T), cells alone (C) and from the medium (M) of each strain.

In the IL1403 Strain:

For the secreted proteins Nuc and Usp-$\Delta_{SP}$Nuc (FIGS. 3 and 4: first three wells), and for the lipoprotein Nlp4-$\Delta_{SP}$Nuc (FIG. 5: first well), a three-band profile is detected, as previously observed in the MG1363 strain (Le Loir et al., 1994; Poquet et al., 1998, abovementioned publications):

a) the band with the highest molecular weight is the precursor from which the signal peptide has not been cleaved, which is confirmed by its presence exclusively in the cells (FIGS. 3 and 4);

b) the intermediate band is the mature form after cleavage of the signal peptide, and, in the case of the secreted proteins Nuc and Usp-$\Delta_{SP}$Nuc (FIGS. 3 and 4), it is present exclusively in the medium;

c) the band with the lowest molecular weight is the NucA peptide which practically comigrates with the commercial NucA form purified from *S. aureus* (the slight difference in migration being due to the different cleavage specificities in *S. aureus* and *L. lactis*), and which is both released into the medium and associated with the cells.

For the Exp5-$\Delta_{SP}$Nuc protein (FIG. 6: first well), two forms are detected only with great difficulty, one having a high molecular weight and one having a low molecular weight, NucA, which practically comigrates with the purified commercial form; there is, therefore, practically total proteolysis in IL1403.

For the AcmA protein (FIG. 7: the first three wells), a four-band profile, as previously observed in the MG1363 strain (Buist et al., 1995, abovementioned publication), is detected:

a) the band with the highest molecular weight is the precursor from which the signal peptide has not been cleaved, which is present exclusively in the cells;

b) the band with a slightly lower molecular weight is the mature form after cleavage of the signal peptide, which is both secreted into the medium and associated with the surface of the cells by affinity for its substrate;

c and d) the two bands of lower molecular weight are active proteolytic products, both secreted into the medium and associated with the surface of the cells by affinity for their substrate.

Figure 5:
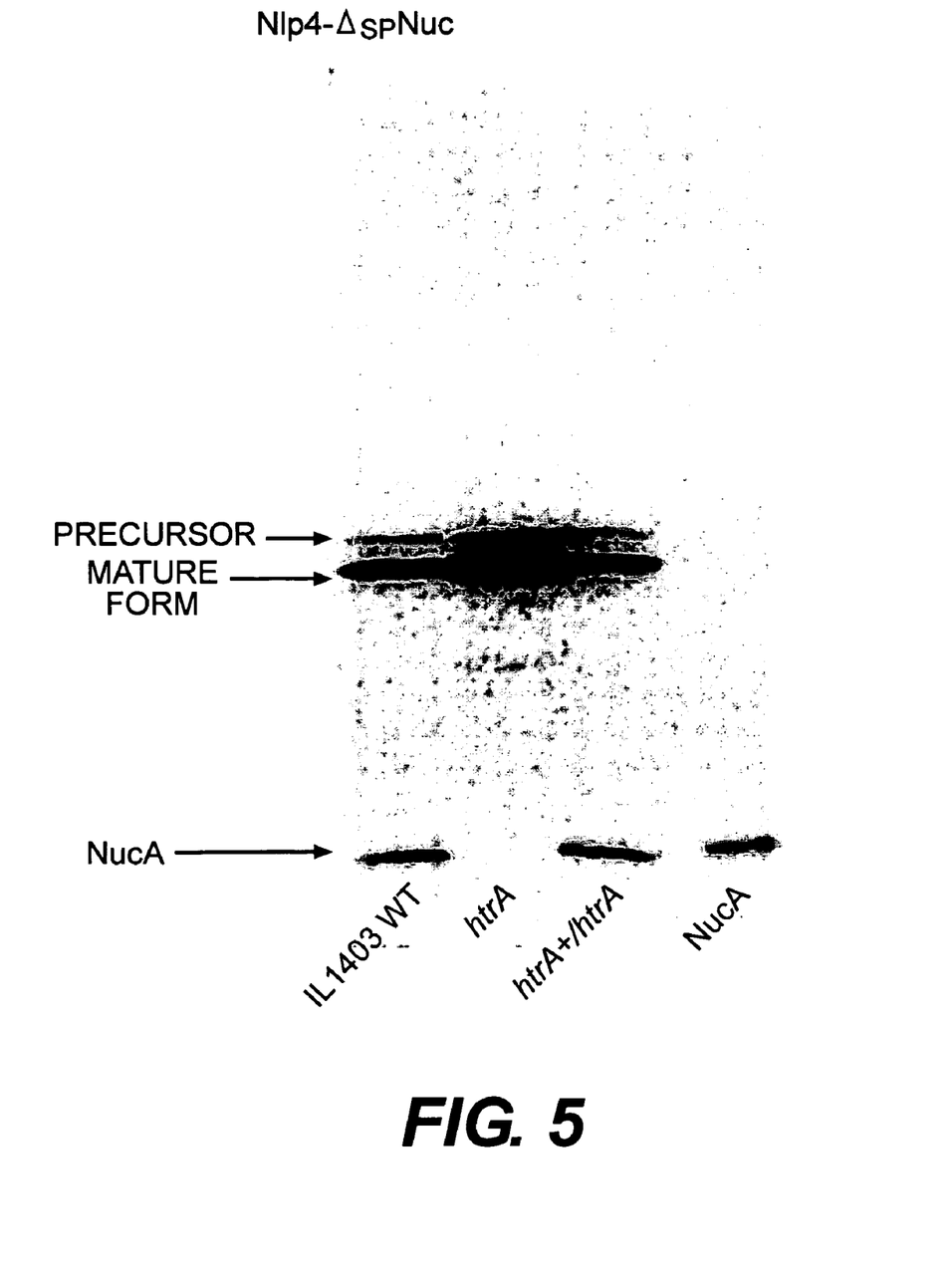
FIG. 5 shows the effect of HtrA$_{L1}$ mutation on the stability of N1p4-Δ$_{SP}$Nuc protein. The degradation profiles of N1p4-Δ$_{SP}$Nuc protein in IL1403 (first well), htrA (central well) and htrA⁺/htrA (last well) strains are shown.
Figure 6:
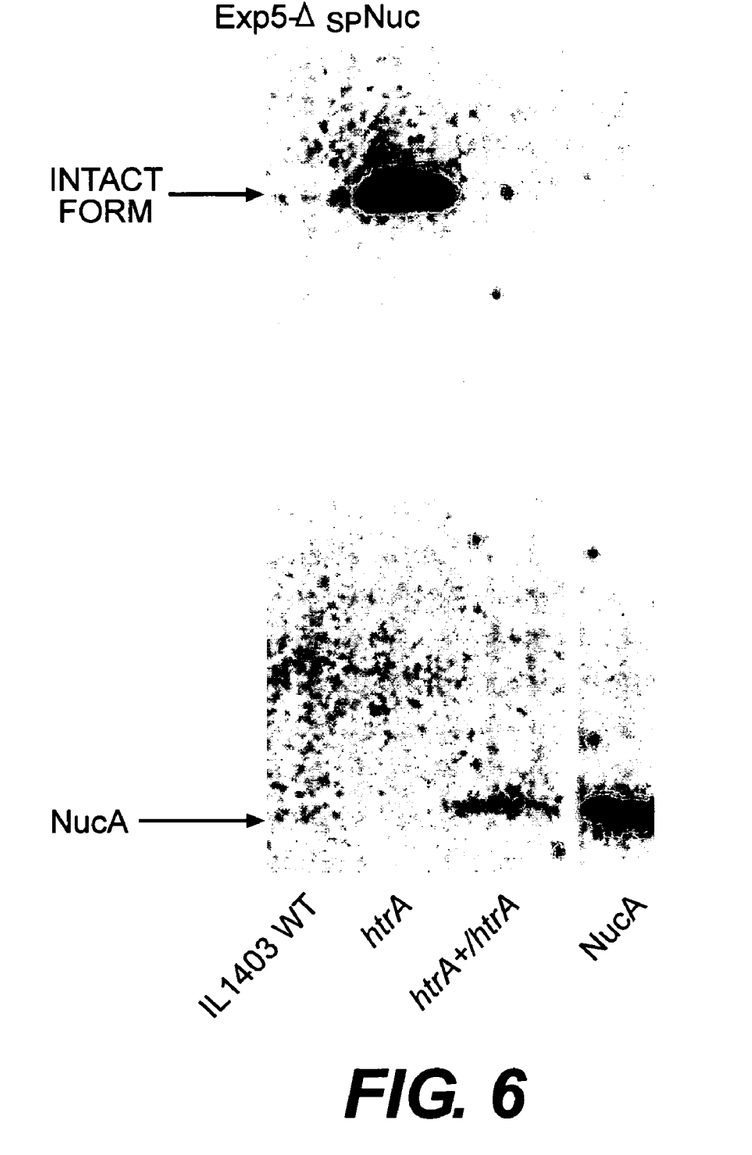
FIG. 6 shows the effect of HtrA$_{L1}$ mutation on the stability of Exp5-Δ$_{SP}$Nuc protein. The degradation profiles of Exp5-Δ$_{SP}$Nuc protein in IL1403 (first well), htrA (central well) and htrA⁺/htrA (last well) strains are shown.

In the htrA$^+$/htrA Strain:

(FIGS. 3 and 4: last three wells, FIGS. 5 and 6: last well, and FIG. 7: last three wells). The profiles observed are absolutely identical to those observed in the wild-type strain. The htrA$^+$/htrA strain therefore exhibits a wild-type proteolytic phenotype which is explained by the wild-type copy of the htrA$_{L1}$ gene which it possesses.

In the htrA Strain:

(FIGS. 3 and 4: three central wells, FIGS. 5 and 6: central well, and FIG. 7: three central wells).

In all cases, none of the proteolytic products are detected; simultaneously, the amount of mature protein (or of high molecular weight protein in the case of Exp5-$\Delta_{SP}$Nuc) increases.

These results show that the product of the htrA$_{L1}$ gene is clearly responsible for the degradation of the secreted proteins, and that its inactivation leads to the complete abolition of this degradation.

What is claimed is:

1. A method of producing a protein of interest, comprising:
providing a *Lactococcus lactis* bacterial strain, wherein the htrA gene has been mutated so that said strain does not express a functional HtrA protease;
introducing into said bacterial strain a nucleic acid having a sequence encoding a protein of interest operably linked to a promoter; and
culturing the bacterial strain under conditions causing expression of the protein from the nucleic acid; recovering said protein exported by said strain in the culture medium.

2. A method according to claim 1, wherein the bacterial strain also does not express a functional PrtP protease.

3. A *Lactococcus lactic* bacterial strain, wherein the htrA gene has been mutated so that said strain does not express a functional HtrA protease, and wherein said strain comprises an expression cassette having a sequence encoding a protein of interest operably linked to a promoter.

4. A bacterial strain according to claim 3, wherein the strain also does not express a functional PrtP protease.

* * * * *

SEQUENCE LISTING

<160> NUMBER OF SEQ ID NOS: 2

<210> SEQ ID NO 1
<211> LENGTH: 1740
<212> TYPE: DNA
<213> ORGANISM: Lactococcus lactis
<220> FEATURE:
<221> NAME/KEY: CDS
<222> LOCATION: (230)..(1453)

<400> SEQUENCE: 1

```
aaacaagatg aaaacatgat ttatcaacat ttttttactt ttttccactt ttctgtggaa      60
aactttatta aaatatccac ttatcctcat taatttttag attatccaca aaaatgtgga     120
gaaactatat tagtttgatt tttgttacta ttaaggtatt attaagtgag agtagatata     180
attacatcat agaaatgcta caaagattaa taattgaaag gaattatttt atg gca aaa     238
                                                        Met Ala Lys
                                                          1 gct aat ata gga aaa ttg cta tta aca ggt gtc gtg ggc gga gcc atc       286
Ala Asn Ile Gly Lys Leu Leu Leu Thr Gly Val Val Gly Gly Ala Ile
      5                  10                  15 gca ctt gga gga agt gca atc tat caa agc act aca aat caa tcg gca       334
Ala Leu Gly Gly Ser Ala Ile Tyr Gln Ser Thr Thr Asn Gln Ser Ala
 20                  25                  30                  35 aat aat agt cgt tca aat aca act agt aca aag gtt agt aac gtt tcg       382
Asn Asn Ser Arg Ser Asn Thr Thr Ser Thr Lys Val Ser Asn Val Ser
                 40                  45                  50 gta aat gtc aat acc gat gtt acc tct gca att gaa aaa gtt tca aat       430
Val Asn Val Asn Thr Asp Val Thr Ser Ala Ile Glu Lys Val Ser Asn
             55                  60                  65 tct gtc gtt tct gtt atg aat tat caa aaa gat aac tca caa agt agt       478
Ser Val Val Ser Val Met Asn Tyr Gln Lys Asp Asn Ser Gln Ser Ser
         70                  75                  80 gac ttc agt tca att ttt ggt gga aat agc ggt tca agt tca tcg act       526
Asp Phe Ser Ser Ile Phe Gly Gly Asn Ser Gly Ser Ser Ser Ser Thr
     85                  90                  95 gat ggc tta cag ctt tct agt gaa ggc tct ggt gtc atc tac aaa aaa       574
Asp Gly Leu Gln Leu Ser Ser Glu Gly Ser Gly Val Ile Tyr Lys Lys
100                 105                 110                 115 tct ggt ggt gat gcc tac gtt gta act aac tac cac gtt att gct ggt       622
Ser Gly Gly Asp Ala Tyr Val Val Thr Asn Tyr His Val Ile Ala Gly
                120                 125                 130 aat agc tca ctt gat gtt ctg ctt tct ggt gga caa aaa gtc aaa gat       670
Asn Ser Ser Leu Asp Val Leu Leu Ser Gly Gly Gln Lys Val Lys Asp
            135                 140                 145 tct gtg gtt ggt tat gat gaa tac aca gac ctt gct gtt ctt aaa atc       718
Ser Val Val Gly Tyr Asp Glu Tyr Thr Asp Leu Ala Val Leu Lys Ile
        150                 155                 160 agt tct gaa cat gtc aaa gat gtg gcg aca ttc gct gat tct agt aaa       766
Ser Ser Glu His Val Lys Asp Val Ala Thr Phe Ala Asp Ser Ser Lys
    165                 170                 175 tta aca att ggt gaa cct gcc att gcc gtt ggc tca cct tta ggt agt       814
Leu Thr Ile Gly Glu Pro Ala Ile Ala Val Gly Ser Pro Leu Gly Ser
180                 185                 190                 195 caa ttt gca aac acc gca act gaa gga att tta tct gca aca agc cgt       862
Gln Phe Ala Asn Thr Ala Thr Glu Gly Ile Leu Ser Ala Thr Ser Arg
                200                 205                 210 caa gtg act ttg acc caa gaa aat ggt caa aca act aat atc aat gca       910
Gln Val Thr Leu Thr Gln Glu Asn Gly Gln Thr Thr Asn Ile Asn Ala
```

-continued

```
                215                 220                 225
att caa aca gat gct gcc att aac cct ggt aac tct gga ggg gct ttg      958
Ile Gln Thr Asp Ala Ala Ile Asn Pro Gly Asn Ser Gly Gly Ala Leu
            230                 235                 240 att aat att gaa gga caa gtt att gga att act caa agt aaa att aca     1006
Ile Asn Ile Glu Gly Gln Val Ile Gly Ile Thr Gln Ser Lys Ile Thr
245                 250                 255 aca act gaa gat ggt tct act tct gtc gaa ggt tta gga ttt gcg att     1054
Thr Thr Glu Asp Gly Ser Thr Ser Val Glu Gly Leu Gly Phe Ala Ile
    260                 265                 270             275 cct tct aat gat gtc gta aat atc att aat aaa ctt gaa gat gat ggt    1102
Pro Ser Asn Asp Val Val Asn Ile Ile Asn Lys Leu Glu Asp Asp Gly
                280                 285                 290 aag att tca cgc cct gct tta ggt atc cga atg gtt gac ctt tca caa    1150
Lys Ile Ser Arg Pro Ala Leu Gly Ile Arg Met Val Asp Leu Ser Gln
            295                 300                 305 tta tca aca aat gac agt tct caa ttg aaa tta cta agc agt gta aca    1198
Leu Ser Thr Asn Asp Ser Ser Gln Leu Lys Leu Leu Ser Ser Val Thr
        310                 315                 320 ggt ggg gtt gtt gtt tac tcc gtc caa tct gga ctt cct gct gcc tca    1246
Gly Gly Val Val Val Tyr Ser Val Gln Ser Gly Leu Pro Ala Ala Ser
325                 330                 335 gct ggt ttg aaa gct gga gat gta att aca aag gtt ggc gat aca gca    1294
Ala Gly Leu Lys Ala Gly Asp Val Ile Thr Lys Val Gly Asp Thr Ala
340                 345                 350                 355 gta acc tct tca aca gac ttg caa agt gct ctt tac tca cac aat atc    1342
Val Thr Ser Ser Thr Asp Leu Gln Ser Ala Leu Tyr Ser His Asn Ile
                360                 365                 370 aat gat aca gta aaa gtt act tat tat cgt gat ggt aaa tca aat aca    1390
Asn Asp Thr Val Lys Val Thr Tyr Tyr Arg Asp Gly Lys Ser Asn Thr
            375                 380                 385 gca gat gtt aaa ctt tct aaa tca acc agt gac tta gaa aca agc agt    1438
Ala Asp Val Lys Leu Ser Lys Ser Thr Ser Asp Leu Glu Thr Ser Ser
        390                 395                 400 cca tct tct tct aat taataactta ataatttaat aaagtcttc tgtaaataga     1493
Pro Ser Ser Ser Asn
    405 aggctttttt catactaaag tctgaaattt ttaaaaataa taaatttcca tttttctttt   1553 attgatttat ggtaaaataa agttaagcat gaaaatttta ctttacttag aagccgaaca   1613 attttttgagt cattcaggaa ttggtcgtgc aatgaaacat caacaacgcg cccttgattt  1673 aatgggcatt gactggacaa aaaatcctga ggatgattac gatatcctcc atttaaatac   1733 ttatggc                                                            1740
```

<210> SEQ ID NO 2
<211> LENGTH: 408
<212> TYPE: PRT
<213> ORGANISM: Lactococcus lactis

<400> SEQUENCE: 2

```
Met Ala Lys Ala Asn Ile Gly Lys Leu Leu Leu Thr Gly Val Val Gly
1               5                   10                  15

Gly Ala Ile Ala Leu Gly Gly Ser Ala Ile Tyr Gln Ser Thr Thr Asn
                20                  25                  30

Gln Ser Ala Asn Asn Ser Arg Ser Asn Thr Thr Ser Thr Lys Val Ser
            35                  40                  45

Asn Val Ser Val Asn Val Asn Thr Asp Val Thr Ser Ala Ile Glu Lys
        50                  55                  60
```

```
Val Ser Asn Ser Val Ser Val Met Asn Tyr Gln Lys Asp Asn Ser
 65                  70                  75                  80

Gln Ser Ser Asp Phe Ser Ser Ile Phe Gly Gly Asn Ser Gly Ser Ser
                 85                  90                  95

Ser Ser Thr Asp Gly Leu Gln Leu Ser Ser Glu Gly Ser Gly Val Ile
            100                 105                 110

Tyr Lys Lys Ser Gly Gly Asp Ala Tyr Val Val Thr Asn Tyr His Val
        115                 120                 125

Ile Ala Gly Asn Ser Ser Leu Asp Val Leu Leu Ser Gly Gly Gln Lys
    130                 135                 140

Val Lys Asp Ser Val Val Gly Tyr Asp Glu Tyr Thr Asp Leu Ala Val
145                 150                 155                 160

Leu Lys Ile Ser Ser Glu His Val Lys Asp Val Ala Thr Phe Ala Asp
                165                 170                 175

Ser Ser Lys Leu Thr Ile Gly Glu Pro Ala Ile Ala Val Gly Ser Pro
            180                 185                 190

Leu Gly Ser Gln Phe Ala Asn Thr Ala Thr Glu Gly Ile Leu Ser Ala
        195                 200                 205

Thr Ser Arg Gln Val Thr Leu Thr Gln Glu Asn Gly Gln Thr Thr Asn
    210                 215                 220

Ile Asn Ala Ile Gln Thr Asp Ala Ala Ile Asn Pro Gly Asn Ser Gly
225                 230                 235                 240

Gly Ala Leu Ile Asn Ile Glu Gly Gln Val Ile Gly Ile Thr Gln Ser
                245                 250                 255

Lys Ile Thr Thr Thr Glu Asp Gly Ser Thr Ser Val Glu Gly Leu Gly
            260                 265                 270

Phe Ala Ile Pro Ser Asn Asp Val Asn Ile Ile Asn Lys Leu Glu
        275                 280                 285

Asp Asp Gly Lys Ile Ser Arg Pro Ala Leu Gly Ile Arg Met Val Asp
290                 295                 300

Leu Ser Gln Leu Ser Thr Asn Asp Ser Ser Gln Leu Lys Leu Leu Ser
305                 310                 315                 320

Ser Val Thr Gly Gly Val Val Tyr Ser Val Gln Ser Gly Leu Pro
            325                 330                 335

Ala Ala Ser Ala Gly Leu Lys Ala Gly Asp Val Ile Thr Lys Val Gly
            340                 345                 350

Asp Thr Ala Val Thr Ser Thr Asp Leu Gln Ser Ala Leu Tyr Ser
            355                 360                 365

His Asn Ile Asn Asp Thr Val Lys Val Thr Tyr Tyr Arg Asp Gly Lys
    370                 375                 380

Ser Asn Thr Ala Asp Val Lys Leu Ser Lys Ser Thr Ser Asp Leu Glu
385                 390                 395                 400

Thr Ser Ser Pro Ser Ser Ser Asn
            405
```